United States Patent [19] [11] 3,972,915
Alt et al. [45] Aug. 3, 1976

[54] N-PHOSPHONOMETHYL GLYCINE PHENYL HYDRAZIDES

[75] Inventors: Gerhard H. Alt, Creve Coeur; Robert W. Street, Kirkwood, both of Mo.

[73] Assignee: Monsanto Company, St. Louis, Mo.

[22] Filed: Aug. 14, 1974

[21] Appl. No.: 497,450

[52] U.S. Cl. ................................ 260/502.5; 71/86; 71/118
[51] Int. Cl.$^2$ ...................... C07F 9/38; A01N 9/36
[58] Field of Search ............ 260/502.5; 71/118, 86

[56] References Cited
UNITED STATES PATENTS

| | | |
|---|---|---|
| 2,859,243 | 11/1958 | Reed .................................. 71/118 |
| 3,223,514 | 12/1965 | Gradsten ........................... 260/502.5 |
| 3,346,397 | 10/1967 | Gortner .............................. 71/118 |
| 3,428,678 | 2/1969 | Trepanier ........................... 71/118 |
| 3,502,685 | 3/1970 | Gevertz et al. ...................... 71/118 |
| 3,516,816 | 6/1970 | Hunter et al. ........................ 71/118 |
| 3,759,909 | 9/1973 | Hageman ............................ 71/118 |
| 3,767,623 | 10/1973 | Alt ..................................... 71/118 |
| 3,799,758 | 3/1974 | Franz ................................ 260/502.5 |
| 3,853,530 | 12/1974 | Franz ................................ 260/502.5 |
| 3,901,679 | 8/1975 | Hofer ................................ 260/502.5 |

*Primary Examiner*—Joseph E. Evans
*Attorney, Agent, or Firm*—Arnold H. Cole; Donald W. Peterson

[57] ABSTRACT

Certain phenyl hydrazides of N-phosphonomethylglycine have been found to be useful as herbicides and plant growth regulators.

13 Claims, No Drawings

N-PHOSPHONOMETHYLGLYCINE PHENYL HYDRAZIDES

This invention relates to a new class of organic chemical compounds. More particularly, this invention is concerned with certain novel derivatives of N-phosphonomethylglycine. The specific derivatives herein are the phenyl hydrazides wherein the ring may be substituted and wherein the terminal nitrogen atom may also contain an alkyl group. This class of compounds has been found to display desirable herbicidal activity when applied to certain varieties of undesirable plants (weeds). Such compounds also produce certain desirable, non-lethal regulatory responses when applied to corn plants.

The novel compounds of the present invention may be represented by the structural formula

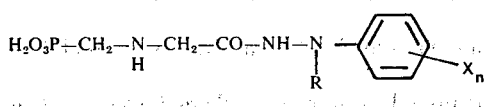

wherein R is hydrogen, methyl or ethyl, $n$ is zero, one or two, and X is methyl, nitro, chlorine or bromine. Preferred compounds are those wherein R is hydrogen.

Compounds of the above formula are prepared by reacting a phenyl hydrazine with an ester or an amide of N-phosphonomethylglycine. In this reaction, it is preferred to use the methyl or ethyl ester in order to facilitate removal of the alkanol by-product. The starting glycinate or glycinamide is obtained in the manner described in U.S. Pat. No. 3,799,758.

The following illustrative, non-limiting examples will further demonstrate to those skilled in the art the manner in which specific compounds of the invention can be prepared.

EXAMPLE I

A mixturwe of 3.66 grams (0.02 mole) of methyl N-phosphonomethyl glycinate and 9.0 grams (0.083 mole) of phenyl hydrazine is charged to a suitable reaction vessel and heated on a steam bath for about 2.5 hours. A viscous red oil forms and is triturated with 50 ml. of ether. An orange crystalline precipitate forms in the ether and is filtered out. The precipitate is then dissolved in 12 ml. of hot acetic acid on a steam bath. A yellow crystalline precipitate is formed and does redissolve redisslve upon addition of 5 ml. of acetic acid. The resultant slurry is quenched with 100 ml. of methanol, permitted to stand for several hours, and finally filtered. After washing with methanol and ether, the product obtained is N-phosphonomethylglycine phenyl hydrazide, m.p. 251°–253°C. (dec.). Elemental analysis shows 41.88% carbon and 5.50% hydrogen as against calculated values of 41.70% and 5.44% for $C_9H_{14}N_3O_4P$.

EXAMPLE II

A mixture of 2.87 grams (0.0157 mole) of methyl N-phosphonomethyl glycinate and 9.7 grams (0.0548 mole) of 2,5-dichlorophenyl hydrazine is heated for about 4 hours at 110°–130°C. The reaction mixture is treated with 75 ml. of ether and filtered. It is the treated with 18 ml. of hot acetic acid on a steam bath, and a thick slurry is formed. This slurry is quenched with 100 ml. of methanol and set aside to cool. The mixture is filtered, and the solids are washed with methanol, and then with 150 ml. of water at reflux temperature. This is followed by filtration, treatment of the solids with hot ethanol, further filtration, and then washing with methanol and ether. The beige powder obtained is air-dried overnight, and the product is N-phosphonomethylglycine 2,5-dichlorophenyl hydrazide, m.p. 273°–275°C. (dec.). Elemental analysis shows 32.75% carbon and 3.67% hydrogen as against calculated values of 32.95% and 3.69% for $C_9H_{12}Cl_2N_3O_4P$.

EXAMPLE III

A mixture of 4.57 grams (0.025 mole) of methyl N-phosphonomethyl glycinate and 12.4 grams (0.102 mole) of 1-methyl-1-phenyl hydrazine is heated for about 6 hours at 120°–145°C. The dark reaction mass is treated with 15 ml. of hot acetic acid on a steam bath and allowed to stand for several days. The semi-solid mass is washed with 100 ml. of methanol and filtered. The solids are treated in boiling water for about 2 hours, cooled and filtered again. The product, obtained as a brown powder, is N-phosphonomethylglycine 2-methyl-2-phenyl hydrazide, m.p. >200°C. (char.). Elemental analysis shows 43.76% carbon, 5.76% hydrogen and 15.34% nitrogen as against calculated values of 43.96%, 5.90% and 15.38% for $C_{10}H_{16}N_3O_4P$.

In a test to demonstrate pre-emergent herbicidal activity, a spectrum of plant species are planted as seeds in a good grade of top soil in an aluminum pan. A solution containing the compound to be tested is sprayed on the soil after planting, and the pan is placed in a greenhouse along with an untreated control pan. Two weeks after treatment, the number of plants of each species in the treated and untreated pans are compared. At an application rate of 5 pounds per acre, the compound of Example III controlled 25–50% of the velvet leaf, lambsquarter, nutsedge and barnyard grass, along with 50–75% of the morning glory. Canada thistle, cocklebur, smartweed, quackgrass, johnson grass and downy brome, the other plant species in the test spectrum were unaffected by the treatment. At the same rate, the compound of Example I controlled substantially all of the johnson grass, but none of the other species, and the compound of Example II displayed no control over the tested plant species.

The same test procedures are followed to demonstrate post-emergent activity except that the plant species are grown in the greenhouse for 2 weeks before treatment, and the application is made to the plant foliage. In this test, the compound of Example III was ineffective at a rate of 10 pounds per acre. With the compound of Example II at 4 pounds per acre, 25–50% control was observed on 6 species, 50–75% control on 2 species and substantially full control on lambsquarter. The smartweed was not present in this test, and no effect was noted on downy brome. The same compound at 10 pounds per acre showed greater control of all test species. Using the compound of Example I in this post-emergent test, control of all plant species at both rates was equal to or better than the control shown by the compound of Example II. Here again, smartweed was not present in the test. The compound of Example I was also tested against another spectrum of plant species, including some of the same plants as the preceeding test, at several lower rates. Significant herbicidal activity was observed at rates of 1.0 and 0.2 pounds per acre, and a limited amount of activity was noted at 0.1 pound per acre.

In order to demonstrate the plant growth regulating activity of compounds of this invention, a number of corn plants of the Pioneer 3567 variety are grown from seeds in an aluminum pan for a period of one week. The height of each corn plant is then measured to the top of the whorl. A 1% solution of a chemical of this invention in acetone is prepared, and a 2.0 ml. portion of said solution is mixed with 0.8 ml. of acetone and 2.8 ml. of a water mixture with 0.05% of Aerosol OT. The resultant solution is then sprayed over the plants in the pan at several application rates. A control pan, planted at the same time as the test pan, also has its plants measured, but receives no chemical application. The pans are transferred to a greenhouse and watered from below in a sand bench. Each pan is fertilized with 40 ml. of a 1.5% solution of Rapid-Gro about 2 days after treatment.

Two weeks after treatment the height of each plant in the pans is again measured to the top of the whorl. After determining the average height increase of the plants in the untreated control pan, it is found that at least two-thirds of the corn plants treated with the compound of Example I show 26% or more stature reduction by direct comparison at application rates of 1.2, 3.0 and 6.0 pounds per acre. The same results are observed with the compound of Example II at the two higher rates. In two tests of this latter compound at rates of 0.6 and 1.2 pounds per acre, the above noted stature reduction was observed in one test but not in the other. Further, the compound of Example III did not produce such stature reduction at a rate of 6.0 pounds per acre.

While the invention has been described herein with regard to certain representative examples for purpose of illustrating its practice, it is not to be construed as limited thereto. Those skilled in the art will readily recognize the variations and modifications which can be made without departing from the spirit and scope of this invention.

What is claimed is:

1. A compound of the formula

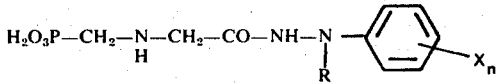

wherein R is hydrogen, methyl or ethyl, $n$ is zero, one or two, and X is methyl, nitro, chlorine or bromine.

2. A compound as defined in claim 1 wherein R is hydrogen.

3. A compound as defined in claim 2 wherein $n$ is zero.

4. A compound as defined in claim 2 wherein $n$ is one.

5. A compound as defined in claim 2 wherein $n$ is two.

6. A compound as defined in claim 5 wherein X is chlorine.

7. A compound as defined in claim 5 wherein X is nitro.

8. A compound as defined in claim 5 wherein X is methyl.

9. A compound as defined in claim 4 wherein X is chlorine.

10. A compound as defined in claim 4 wherein X is methyl.

11. A compound as defined in claim 2 wherein $X_n$ is 2,5-dichloro.

12. A compound as defined in claim 1 wherein R is methyl.

13. A compound as defined in claim 12 wherein n is zero.

* * * * *